United States Patent [19]
Martin

[11] Patent Number: 4,731,019
[45] Date of Patent: Mar. 15, 1988

[54] DIAMOND COATED SCALER DENTAL INSTRUMENT FOR ULTRASONIC OPERATION

[76] Inventor: Howard Martin, 909 Pershing Dr., Silver Spring, Md. 20910

[21] Appl. No.: 861,292

[22] Filed: Apr. 9, 1986

Related U.S. Application Data

[63] Continuation of Ser. No. 616,843, Jun. 4, 1984, abandoned, which is a continuation-in-part of Ser. No. 439,724, Nov. 8, 1982, abandoned.

[51] Int. Cl.$^4$ .................................................. A61C 1/07
[52] U.S. Cl. ...................................... 433/119; 433/166; 433/125; 51/59.55
[58] Field of Search ................. 433/86, 118, 119, 142, 433/166, 125; 128/24 A; 51/59.55; 74/1.55

[56] References Cited

U.S. PATENT DOCUMENTS

| | | | |
|---|---|---|---|
| D. 261,932 | 11/1981 | Bussiere | 433/119 |
| 959,054 | 5/1910 | Glover | 433/166 |
| 2,453,696 | 11/1948 | Brooks | 433/165 |
| 2,562,587 | 7/1951 | Swearingen | 433/166 |
| 2,697,878 | 12/1954 | Oberley | 433/166 |
| 2,735,181 | 2/1956 | Carpenter | 433/166 |
| 2,831,132 | 4/1958 | Jackson | 433/119 |
| 2,874,470 | 2/1959 | Richards | 128/24 A |
| 2,990,616 | 7/1961 | Balamuth et al. | 433/119 |
| 3,133,351 | 5/1964 | Von Seggern | 433/119 |
| 3,368,280 | 2/1968 | Friedman et al. | 51/59.55 |
| 3,645,255 | 2/1972 | Robinson | 128/24 A |
| 3,930,173 | 12/1975 | Banko | 433/119 |
| 4,270,903 | 6/1981 | Nash | 433/165 |
| 4,283,175 | 8/1981 | Nash | 433/119 |
| 4,332,558 | 6/1982 | Lustig | 433/119 |
| 4,353,696 | 10/1982 | Bridges | 433/119 |

FOREIGN PATENT DOCUMENTS 1954272  5/1970  Fed. Rep. of Germany ...... 433/119

*Primary Examiner*—John J. Wilson
*Attorney, Agent, or Firm*—Walter G. Finch

[57] ABSTRACT

The invention is an improved dental instrument for scaling by ultrasonic operation. The scaler is coated with diamond particles to overcome the patient discomfort associated with the prior art chipping and dislodgement procedures. Four unique and novel scaler configurations are provided for various aspects of dental work, each is diamond coated and fitted for ultrasonic operation at lower power settings than present prior art instruments.

3 Claims, 12 Drawing Figures

DIAMOND COATED SCALER DENTAL INSTRUMENT FOR ULTRASONIC OPERATION

This patent application is a continuation of application Ser. No. 616,843, filed June 4, 1984, now abandoned, which is a continuation-in-part of application Ser. No. 439,724, filed Nov. 8, 1982, now abandoned.

BACKGROUND AND SUMMARY OF THE INVENTION

The invention relates to dental instruments and in particular to dental instruments used for periodontal disease. Specifically, the invention relates to scaler dental instruments that are diamond coated for treating periodontal disease, the instruments being operated by low powered ultrasonic devices.

The use of an ultrasonic generator for operative dentistry has been in use for some time. Some attempts have been made at adapting the ultrasonic generator to periodontal techniques. Such use has increased over the years, however, the developments have only been in improved generators and irrigation techniques and design. There have been no changes in the prior art actual dental instruments that go with ultrasonic device and the irrigation means in more than a quarter of a century.

In the prior art the ultrasonic instruments have been routinely used for scaling, curettage, root planing, and overhang removal. More limited use, in most cases non-use, has been in applications for mucogingival surgery and gingivoplasty.

The present prior art instruments are blunt, dull, and rounded, and merely chip away at the root surface due to the ultrasonic vibrations, a knocking and hammering action, via an elliptical motion at the end of the instrument. This operation has been referred to as scraping the tooth.

There are a variety of interchangeable tip designs for specific applications due to the variegation of tooth form. All such tip designs, however, have a dull rounded edge and no real cutting edges or cutting means affixed to the instrument. Rotary type instruments are not feasible for this work on the root surface and when used on bone have bad deleterious effects as has been shown in microscopic cell studies.

Periodontal disease is a chronic disease that produces deformities with the periodontium (the gum, bone, and root areas). Hyperplasia manifestations and crippling bony defects due to accretions on root surfaces, and infected soft tissue responses to these accretions are aspects of the disease.

Periodontal pockets are spaces bordered on one side by calcified structures of the tooth and root, the lateral side by gingival epithelium covering the alveolar jaw bone.

The basic tenet of periodontal treatment is to smooth and plane the root surface, remove the pocket and contour the bone to physiologic supportive form. The pocket is removed of the infected tissue by curettage of the inner aspect. This all implies a spatial relationship which has a direct bearing on the deformities and requires an instrument to achieve a remodeling, contouring, and cleansing removal of the afflicted area. The prior art instruments have not been capable of performing this special work with the degree of accuracy and improvement that is required for good periodontal treatment.

The present invention has many improved advantages over the prior art instruments. The diamond coated instrument is stronger, due to the diamond coating. The present invented instrument is useable at a lower power setting on the ultrasonic generator, thus causing less vibration. The diamond coated scraper instrument cuts by abrading rather than chipping or dislodgement, which makes patient comfort superior and the dentist's fatigue less. The four embodiments of the dental instrument are each novel and unique in that they have been carefully thought out intellectually in the inventive process to have the right angles and bends and the right configuration for each of the precise periodontal treatment operations that the dentist must perform.

Hand curettage in the prior art left a smoother surface on the root of tooth than present ultrasonic instruments, this is due to chipping and fracturing of the surface. The diamond coated instruments of the present invention alleviate this problem.

Thus, the present invention is more effective, safer, and more economical, and reduces the dentist's armentarium of necessary instruments, because the dental instruments of the present invention are multipurposeful.

The soft tissue side of the periodontal lesion is curetted by the diamond instrument and removes the inflamed, necrotic tissue. In the prior art, the present ultrasonic tips being blunt, dull, and rounded cannot adequately curette soft tissue. This is a unique feature of the present instruments of the invention, the economy of instrumentation is that the diamond coated instruments are multipurpose. They are used for the root surface, soft tissue, and bone and are effective in all those uses. There is, therefore, less fatigue for the operator and for the patient.

In the prior art previous to the present invention, the debrided root materials acted as an abrasive slurry in polishing the root surface. This slurry is usually a bacterial contaminated material and may act to insinuate necrotic material and bacteria into the nicks and grooves on the root surface and in the soft tissue aspect.

With the present invention no slurry is involved as the sharp fine cutting surface of the present invention continually removes the root surface toxins due to the abrasive action of the four embodiments of the present invented tool.

In addition, the prior art slurry method used the slurry to polish the root, a very poor technique. The present invention eliminates this by accomplishing the polishing without the contamination hazard.

The typical infrabony defect, found in such diseased dental problems, is exceptionally well treated by each embodiment of the instrument of the present invention. Such defects lie within the alveolar bone and the epithelial attachment resides within the defect on the cemental/dentin root surface side. The sharp fine cutting surface of the present invention can plane and abrade the cementum/dentin, and curette and contour the gingival tissue and alveolar bone.

The sharp fine cutting surface of the present diamond scaler instrument, under ultrasonic vibration, reduces the physical exertion required with the prior art dull and incorrectly configured instruments, even under ultrasonic operating conditions. Note that the incorrectly configured instruments of the prior art has been and is a major problem in effective periodontal treatment.

The present invention, applied with a very light, feather-like touch, produces faster and more effective results. In addition, there is an increase in patient comfort due to the lighter stroke. The sharp fine cutting surface of the diamond scaler instrument of the present invention is exceptionally efficient against hard tissue surfaces (cementum, dentin and bone). This is particularly true in such dental operations as scaling and root planing procedures as the present invention abrades rather than chipping and knocking when cutting the surface.

The present invention is also useful against the alveolar bone (osteoplasty) to contour and shape as well as to remove necrotic bone (osteectomy). This is all accomplished by the same instrument of the present invention. In the prior art, the dentist switches to a rotary diamond stone bur to accomplish the bony work. Although the rotary procedure produced a reasonably smooth surface cut in the bone, the procedure resulted in a very slow healing rate, actually the slowest healing rate of any tried procedure. The present invention combines the two desirable objectives, a smooth cut and fast healing.

Operator derived motion and force, as with hand instruments, to correct bone and root defects is obviated. The bulkier rotary handpieces cannot be placed by the dentist with the exactitude of the present invention. This is particularly true because of the exact angles, specific bends, and unique and novel configurations of each of the four embodiments, all of which permits the periodontest to perform the dental operations with a scientific exactitude not possible with prior art instruments. Furthermore, the enhanced cutting ability of the present invention allows for precise control of the mechanical energy to the instrument for a precision cut. The diamond particles transmit the ultrasonic wave precisely and repetitively without damage to itself. This does not occur with the usual prior art ultrasonic instrument which begins to pit after limited usage.

The diamond scaler instrument of the present instruments of the invention are capable of removing mineralized tissues with great ease and efficiency. This is a time saver, incorporating all necessary procedures in the four embodiments of the one type of instrument which is not available in the prior art. The full ultrasonic instrument of the prior art is not used for the bony work. Thus, the present invention treats the root surface, the soft tissue, and the bony wall expeditiously and without having to change instruments as in the prior art.

The prior art tips cause excess vibration when used in an ultrasonic operation because of the necessary high power input, thus, heat is generated and patient discomfort increases. The prior art tips also break due to the high power action. The present invention overcomes this.

When using the prior art instruments for a dental treatment where scaling, cleansing and curettage is necessary, it is not unusual to have more than a dozen instruments available for alternate ready use. The present invention of the few instruments illustrated provides a capability for all these operations in accomplishing the task. As noted hereinbefore, the prior art instrumentation for ultrasonic use does an unsatisfactory job at root planing, even poorer than hand instruments, removes less calculus than hand instruments. When the prior art instruments are used with greater force to compensate for the deficiencies, damaged root surfaces occur.

The prior art rotary instruments mentioned hereinbefore often shred the soft tissue, requiring surgical scissors to trim the damaged tissue. The present invention overcomes this problem. There isn't any tactile sense present with rotary instruments. Neither is there a good tactile sense of "feel" with a dull ultrasonic instrument or even with a sharp tipped hand instrument. As a result, the ability to remove all accretions and necrotic epithelium is usually not achieved by the prior art ultrasonic instrumentation or by hand instruments. Such deficiencies in the prior art often require a second reentry.

Other areas in the prior art, in which the present invention does a precise and controllable job, are restorations and overhangs and stain removal on teeth. In the case of the restorations and overhangs, the rotary and prior art ultrasonic instruments nick, gouge and chip, thus producing concavities and irregular surfaces.

Thus, the improvements provided in the present invention are a combination of the diamond coated surfaces, the specifically defined angles and defined bends, and the unique and novel configuration presented by these angles and bends to reach specific locations or positions and unique and novel configuration of the operating end of each of the four embodiments of the invention.

It is, therefore, an object of this invention to provide a plurality of diamond coated scaler dental instruments for ultrasonic operation.

It is also an object of this invention to provide diamond coated scaler dental instruments that can be used at a lower power ultrasonic input.

It is another object of this invention to provide diamond coated scaler dental instruments which are all purposeful to reduce the number of dental instruments required to perform dental operations.

It is still another object of this invention to provide diamond coated scaler dental instruments to reduce patient discomfort and operator fatigue.

It is yet another object of this invention to provide diamond coated scaler dental instruments that leave a smooth surface on the tooth structure without chipping, gouging, or fracturing.

It is yet still another object of this invention to provide diamond coated scaler dental instruments that may be used on tooth structures, bones, and soft tissue of the mouth.

It is also still another object of this invention to provide diamond coated scaler instruments that each have a unique and novel combination of angles, bends, and shapes so that each forms a configuration particularly adapted to a specific periodontal operation treatment.

Further objects and advantages of the invention will become more apparent in light of the following description of the preferred embodiments.

DESCRIPTION OF THE PREFERRED EMBODIMENTS

Figure 1:
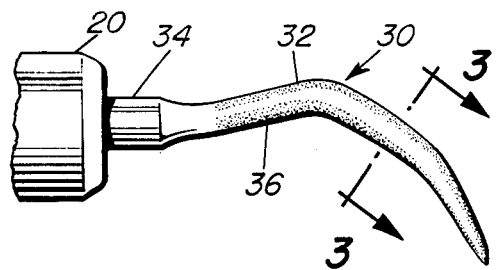
FIG. 1 is a side view of a first embodiment of a diamond coated scaler dental instrument.
Figure 4:
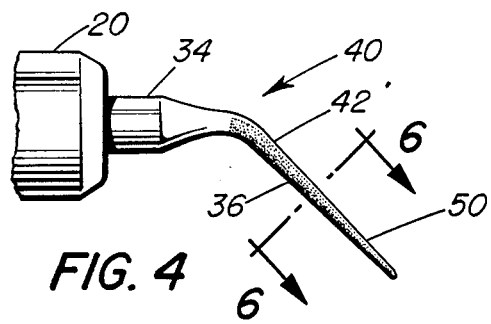
FIG. 4 is a side view of a second embodiment of a diamond coated scaler dental instrument.
Figure 5:
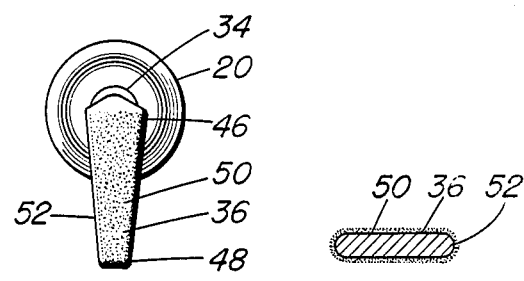
FIG. 5 is an end view of FIG. 4.
Figure 7:
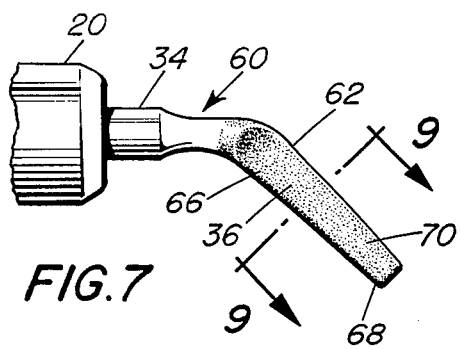
FIG. 7 is a side view of a third embodiment of a diamond coated scaler dental instrument.
Figure 10:
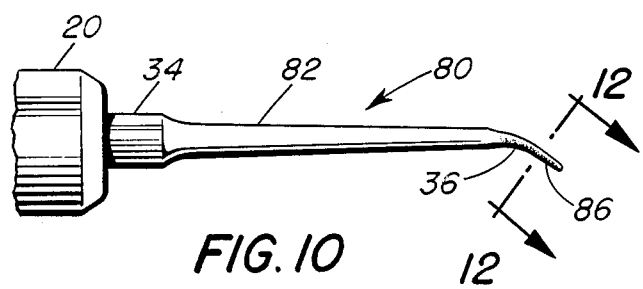
FIG. 10 is a side view of a fourth embodiment of a diamond coated scaler dental instrument.

Referring now to the drawings and particularly to FIGS. 1, 4, 7, and 10: a first embodiment of a diamond coated scaler dental instrument is shown at 30 in FIG. 1; a second embodiment of the scaler instrument is shown at 40 in FIG. 4; in FIG. 7 a third embodiment of the scaler instrument is shown at 60; and in FIG. 10 a fourth embodiment of the diamond coated scaler instrument is shown at 80.

Figure 2:
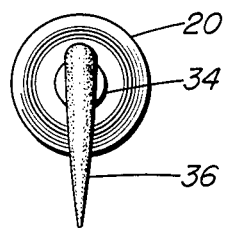
FIG. 2 is an end view of FIG. 1.

End views of the four embodiments are shown in FIGS. 2, 5, 8, and 11; FIG. 2 for the first embodiment, FIG. 5 for the second embodiment, FIG. 8 for the third embodiment, and FIG. 11 for the fourth embodiment.

Figure 3:
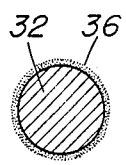
FIG. 3 is a cross sectional view on line 3—3 of FIG. 1.

Cross sectional views through the working ends of the four embodiments of the diamond coated scaler dental instrument are shown in FIGS. 3, 6, 9, and 12; FIG. 3 for the first embodiment, FIG. 6 for the second embodiment, FIG. 9 for the third embodiment, and FIG. 12 for the fourth embodiment.

Turning now to a detailed description of each of the four embodiments of a diamond coated scaler dental instrument, the four embodiments will be described in sequence. All four embodiments removably fit into a common ultrasonic instrument holder 20 which is part of an ultrasonic wave generating system. Only the end of the ultrasonic instrument holder 20 is shown in the drawings. For illustration purposes, the end of the ultrasonic instrument holder 20 represents the entire ultrasonic system which generates the ultrasonic waves that are conducted to the four embodiments of the diamond coated scaler dental instrument 30, 40, 60, and 80 through the ultrasonic instrument holder 20.

The first embodiment of a diamond coated scaler dental instrument 30 has a hook-like working body 32. The hook-like working body 32 has a mounting end 34 for removably affixing the instrument 30 to the holder 20 in a ridged manner. The hook-like working body 32 is coated with diamond particles 36 over most of its surface, as can be seen by shading on the hook-like working body 32 in FIGS. 1 and 2. The diamond coating 36 actually strengthens the hook-like working body 32.

The hook-like working body 32 is particularly configured to provide easy introduction into and around the tooth being treated. Note as the hook-like working body 32 leaves the mounting end 34 in a short horizontal portion in line with the mounting end 34, it is then canted slightly upward, then bent to an angle of approximately 45° to start a downward slope, and at approximately the half-way point to the distal end (from that original bend) it is further bent downward to form the pointed hook-like end. The total curvature from the original portion canted slightly upward, is slightly less than 90°. The specific angles and bends in the included angle between the original portion canted slightly upwardly and the pointed end being slightly more than 90° were developed by experimentation in order to provide a specific motion as described in detail hereinafter.

The total hook-like configuration of slightly less than 90°, together with the specific bends and resulting configuration, results in a final ultrasonic motion of the instrument, when under an ultrasonic impulse, of a planing type of action. At 90° or more the action tends to knock or rap the patient where the instrument was applied and is the reason the special configurations were invented. Thus, the hook-like working body 32 has a unique and novel configuration, unlike the prior art devices, which enhances the operational use.

The distal end of the hook-like working body 32 is tapered and pointed, as can be seen in FIGS. 1 and 2 and was specifically developed, so that the ultrasonic vibration can be transmitted to a very small point of a tooth or soft tissue needing treatment. This is especially effective with the diamond coating 36 covering the pointed end as well and because of the low power applied as described hereinbefore.

The total diamond coating 36 coverage of the hook-like configuration can be seen in FIG. 3. The cylindrical configuration of the hook-like working body 32, seen in cross-section in FIG. 3, provides added strength where prior art instruments have been breaking.

Turning now to the second embodiment of a diamond coated scaler-dental instrument 40, it has the same type of mounting end 34 as the first embodiment.

The second embodiment of the diamond coated scaler dental instrument 40 has a blade-like body 42 that is slightly tapered in two directions, but is not pointed. Note that the blade-like body 42 tapers from a wide end 46 at the juncture with the projecting portion from the cylindrical mounting end 34, to a narrow end 48 at the distal end of the blade-like body 42, which can be seen in FIG. 5. In a like manner, the blade-like body 42 also tapers in its thickness, which can be seen in FIG. 4, from its thickest part at the wide end 46 to its thinnest part at the narrow end 48.

Figure 6:
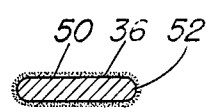
FIG. 6 is a cross sectional view on line 6—6 of FIG. 4.

The blade-like body 42 is bent downwardly from a horizontal portion at approximately 45° from the axis of the cylindrical mounting end 34. The top and bottom sides 50 are flat, and the edges 52 are all rounded. The flat sides 50 and the rounded edges 52 are best seen in FIG. 6.

The diamond coating 36 covers literally all of the blade-like body 42. This can be seen in FIGS. 4, 5, and 6, however, FIG. 6 illustrates how the diamond coating completely surrounds the blade-like body 42. Here again, the diamond coating 36 adds strength to the blade-like body 42.

The blade-like body 42 bend and configuration was developed by experimentation as the most useful configuration for dental operations on teeth adjacent to the cheek and tongue in order to properly reach those points in periodontal operation treatments. Prior art instruments did not provide this facility for a periodontal dentist particularly regarding the shocking knocking and rapping when using the prior art instruments.

Turning now to the third embodiment of a diamond coated scaler dental instrument 60, the instrument has a body configuration that is somewhat the reverse of the second embodiment. The configuration is a knife-like body 62, also tapered in two directions similar to the second embodiment as can be seen in FIGS. 7 and 8.

The knife-like body 62 also is bent downwardly at approximately 45° from the axis of the cylindrical mounting end 34. The sides taper from a wide end 66 to a narrow end 68, as can be seen in FIG. 7.

Figure 8:
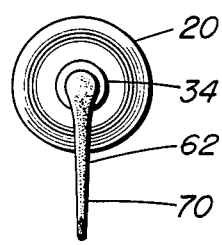
FIG. 8 is an end view of FIG. 7.

The knife-like body 62 also tapers in its thickness, as can be seen in FIG. 8, from the thickness part at the wide end 66 to its thinnest part at the narrow end 68.

Figure 9:
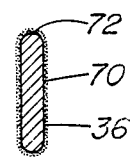
FIG. 9 is a cross sectional view on line 9—9 of FIG. 7.

The fact that the knife-like body 62 is more or less the reverse of the blade-like body 42 can be seen by comparing FIGS. 9 and 6, respectively.

The knife-like body 62 has flat sides 70 and rounded edges 72, as can best be seen in FIG. 9.

The knife-like body 62 is literally all covered with the diamond coating 36 as can be observed in FIGS. 7, 8, and 9, however, FIG. 9 illustrates how the diamond coating completely surrounds the knive-like body 62.

The third embodiment of the diamond coated scaler dental instrument 60 was developed at the specific bend and in the specific knife-like configuration so as to be useful in slotted areas or crack-like openings where the instrument must enter knife-like. Prior art instruments did not provide the facility for this bend of periodontal operation treatment. In a like manner, the third embodiment of the present invention also operates without the knocking or rapping of the prior art devices.

The fourth embodiment of the diamond coated scaler dental instrument 80 is particularly useful in reaching teeth that are not readily accessible. Coupled with the first embodiment, the two instruments can easily reach any location of teeth to perform dental operations. These two configurations were specifically developed in the invention because prior art instruments did not present such a cooperative combination.

The fourth embodiment of the diamond coated scaler dental instrument 80 has an elongated and slender shank-like body 82 with the distal end formed into the short end bend 86 bent slightly downward from the shank-like body 82. The slightly bent end 86 is set at an angle of less than 45° to the axis of the shank-like body 82.

The axis of the shank-like body 82 is a continuation of the axis of the mounting end 34. The shank-like body 82 tapers, cone-like, along its axis from its widest part adjacent to the mounting end 34 to its narrowest part at its juncture with the bent down end 86.

Figure 11:
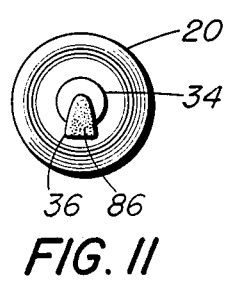
FIG. 11 is an end view of FIG. 10.
Figure 12:
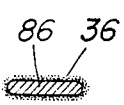
FIG. 12 is a cross-sectional view on line 12—12 of FIG. 10.

The bent down end 86 is flattened out into a more or less claw-like configuration as can be seen in FIG. 11. The claw-like configuration tapering from a narrow end, integral with the narrowest part of the tapered shank-like body 82, to a wide end at the distal end of the bent down end 86. The bent down end 86 also tapers in its thickness from the point where it is integral with the narrowest part of the tapered shank-like body 82, to its distal end where it is thinnest as can be seen in FIG. 12.

Only the bent down end 86 is diamond coated on the fourth embodiment of the diamond coated scaler dental instrument 80. The bent down end 86 is substantially totally covered with the diamond coating as can be seen in FIGS. 10, 11, and 12. FIG. 12 indicates how the bent down end 86 is completely surrounded by the diamond coating 36. As noted hereinbefore, the fourth embodiment of the invention together with the first embodiment of the invention permits access to teeth that are not readily accessible. The particular configuration and angle of bend of the fourth embodiment of the invention was developed to provide a wider operational surface area than the first embodiment of the invention when used in periodontal operation treatments.

The diamond grit can be varied from a course to a fine size on specific instruments so as to provide a range of cutting mediums. The range will assist in selections for specifically easy or stubborn resistance in removing calcareous particles (such as calculus, tartar, and cemental projections), granulation tissue, and spicules. The fine grit can be used to smooth and polish the root surface which is the necessary final step on the root while also burnishing the bone to a smooth confluent form necessary on both sides for a healing physiologic response.

The diamond particles can be plated, coated, swedging sintered, or bonded or impregnated into the metal surface of the tip. The tips may be stainless steel or other suitable metal.

The irrigation flow, used in such dental operations, cleans off the asperities and flushes the debris away.

The power to accomplish results with the four embodiments of the diamond coated scaler dental instrument is a lower setting on the power generator of the ultrasonic means. This is because of the increased effectiveness of the diamond coated instrument and the unique and novel configuration of the instrument operating ends.

The scaling instruments, which in the case of the present invention may also be used as curettage instruments, serve the following purposes;

1. Removal of calcified deposits from the crown and root surface of the tooth.
2. Removal of necrotic, altered cementum from the subgingival root surface.
3. Debridement of the soft tissue lining of the pocket.

The four embodiments of the present invention replace the plurality of instruments used in the prior art of manual operations and the prior art of ultrasonic operations.

Specifically, the four embodiments of the present invention have a capability for the removal of supragingival calculus and stain, subgingival scaling, root planing, removal of infected soft tissue linings, and removal or tenacious subgingival calculus and necrotic cementum. This is a distinct advantage over the plurality of prior art instruments which are necessary for the same operational treatment and, in addition, eliminates the shock of the knocking and rapping of the prior art instruments.

The first embodiment of the present invention is a most important instrument, it is particularly efficient with the diamond coating. The diamond coating is better for adaptation of ultrasonic means of powering the instruments. The problems associated with applying ultrasonic power to the prior art instruments has been covered hereinbefore.

One particular advantage is that the diamond coated embodiments of the present invention abrades in all directions due to the all around diamond coating and the novel and unique configuration of the four embodiments which has been described for specific periodontal operation treatments. This allows the instruments to cut in all directions and on all aspects and sides. Pressure by the operator is reduced, and the number of strokes to achieve a proper smoothing and cleansing are reduced because of the improved effectiveness of the instrument.

The present invention also improves operations where restorations and overhangs are concerned (amalgam, gold crowns, acrylics, cements, and other such conditions), as these substances are irritants to the periodontal tissues. It is important that these items be polished flush with the tooth surface and contoured. With the present invention this is possible, whereas with the prior art knocking and rapping and the poorly configured instrument ends, such refined dental operation processes were not practical.

The embodiments of the diamond coated scaler dental instruments is a precise and controllable instrument, whereas the prior art instruments are not. At present in the prior art the procedure is to keep ultrasonic tips away from the bone to avoid necrosis and sequestration. This is not a problem when using the instruments of the present invention.

As can be readily understood from the foregoing description of the invention, the present structure can be configured in different modes to provide the ability to perform dental operations.

Accordingly, modifications and variations to which the invention is susceptible may be practiced without departing from the scope and intent of the appended claims.

What is claimed is:

1. A dental instrument suitable for affixing to a holder means, such as an ultrasonic device, comprising:
   a mounting portion, said mounting portion being suitable for being removably affixed to a holder means;
   an instrument portion, said instrument portion being integral with and a continuation of said mounting portion, said instrument portion having the distal end thereof further configured for dental-type operations, said distal end of said instrument portion being hook-like in configuration with a conical pointed end as a specific configuration thereof, said hook-like configuration in a vertical plane through the longitudinal axis thereof being configured from a first horizontal section thereof as an axial extension of said mounting portion, to a second section canted slightly upward from said first horizontal section, thence to a third section bent downwardly at an approximate angle of 45° to the axis of said second section, then to a fourth section being further bent downwardly at less than 45° from said third section, the cross-sectional configuration of said hook-like configuration being cylindrical with the extreme distal end of said fourth section tapering to a point; and
   a plurality of abrasive particles, said abrasive particles being diamond particles, said diamond particles being available in a plurality of relative sizes, said diamond particles being suitably affixed to enclose said distal end and to surround said second, third and fourth sections of said instrument portion configured for said dental-type operations.

2. A dental instrument suitable for affixing to a holder means, such as an ultrasonic device, comprising:
   a mounting portion, said mounting portion being suitable for being removably affixed to a holder means;
   an instrument portion, said instrument portion being integral with and a continuation of said mounting portion, said instrument portion having the distal end thereof further configured for dental-type operations, said distal end of said instrument portion being blade-like in configuration as a specific configuration thereof, said blade-like configuration in a vertical plane through the longitudinal axis thereof is configured from a first horizontal section thereof as an axial extension of said mounting portion, from which a second section is bent downwardly at an approximate angle of 45° to the axis of said first section, said second section being flattened in a transverse direction to said vertical plane, said flattened section being tapered in two directions, one of said tapers being of the thickness of said flattened section, said taper of said thickness being thickest at point where said bend downward is made and thinnest at the distal end of said second section, the other taper being of the flattened section in said transverse direction, said taper in transverse direction being widest at the end where said bend downward is made, and narrowest at the distal end of said second section, the edges of said flattened section being rounded; and
   a plurality of abrasive particles, said abrasive particles being diamond particles, said diamond particles being available in a plurality of relative sizes, said diamond particles being suitably affixed to enclose said distal end and to surround said second section of said instrument portion configured for said dental-type operations.

3. A dental instrument suitable for affixing to a holder means, such as an ultrasonic device, comprising:
   a mounting portion, said mounting portion being suitable for being removably affixed to a holder means;
   an instrument portion, said instrument portion being integral with a continuation of said mounting portion, said instrument portion having the distal end thereof further configured for dental-type operations, said distal end of said instrument portion being knife-like in configuration as a specific configuration thereof, said knife-like configuration in a vertical plane through the longitudinal axis thereof is configured from a first horizontal section thereof as an axial extension of said mounting portion, from which a second section is bent downwardly at an approximate angle of 45° to the axis of said first section, said second section being flattened in the direction of said vertical plane through said longitudinal axis of said instrument portion, said flattened second section being tapered in two directions, one of said tapers being of the thickness of said flattened section, said taper of said thickness being thickest at point where said bend downward is made and thinnest at the distal end of said second section, the other taper being of the flattened section in said vertical plane, said taper in vertical plane being widest at the end where said bend downward is made and narrowest at the distal end of said second section, the edges of said flattened second section being rounded; and
   a plurality of abrasive particles, said abrasive particles being diamond particles, said diamond particles being available in a plurality of relative sizes, said diamond particles being suitably affixed to enclose said distal end and to surround said second section of said instrument portion configured for said dental-type operations.

* * * * *